US00PP25862P3

(12) United States Plant Patent
Goffreda et al.

(10) Patent No.: US PP25,862 P3
(45) Date of Patent: Sep. 8, 2015

(54) APRICOT TREE NAMED 'NJA151'

(50) Latin Name: ***Prunus armeniaca* L.**
Varietal Denomination: NJA151

(71) Applicant: Rutgers, The State University, New Brunswick, NJ (US)

(72) Inventors: Joseph C. Goffreda, Millstone Township, NJ (US); Anna M. Voordeckers, East Windsor Township, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 285 days.

(21) Appl. No.: 13/694,820

(22) Filed: Jan. 8, 2013

(65) Prior Publication Data

US 2014/0196181 P1 Jul. 10, 2014

Related U.S. Application Data

(60) Provisional application No. 61/631,543, filed on Jan. 8, 2012.

(51) Int. Cl.
*A01H 5/08* (2006.01)

(52) U.S. Cl.
USPC ..... Plt./186
CPC ..... *A01H 5/0843* (2013.01)

(58) Field of Classification Search
USPC ..... Plt./186
CPC ..... A01H 5/0843; A01H 5/0837
See application file for complete search history.

*Primary Examiner* — Kent L Bell
(74) *Attorney, Agent, or Firm* — James A. Lucas; Driggs, Hogg, Daugherty & Del Zoppo Co., LPA

(57) ABSTRACT

A new and distinct apricot variety of *Prunus persica* named 'NJA151' is provided. This variety is distinguished from other apricot varieties by its unique combination of showy flowers, fruit that ripen in early season, attractive fruit with a dark orange ground color, freestone fruit with a moderately juicy, fine, melting texture and moderately acidic flavor, and good production of fruit.

6 Drawing Sheets

Latin name of genus and species of the plant claimed: *Prunus armeniaca* L.

CROSS REFERENCE TO RELATED APPLICATIONS

None

STATEMENT REGARDING FEDERALLY SPONSORED RESEARCH OR DEVELOPMENT

None

BACKGROUND OF THE INVENTION

The present invention relates to a new and distinct variety of apricot tree named 'NJA151'. Our new tree resulted from crossing 'Harcot' as the seed parent with 'Bhart' apricot tree, as the pollen parent. The new variety differs from seed parent 'Harcot' (unpatented) in that the new variety produces fruit with a dark orange ground color in late June, while the seed parent produces fruit with orange ground color in early July. The new variety differs from pollen parent 'Bhart' (Unpatented in the US) in that the new variety is more productive, while the pollen parent has cropped inconsistently. The resulting tree was selected when growing in a cultivated area as the $107^{st}$ tree in the $21^{th}$ row of Block J at a research farm in Cream Ridge, N.J.

BRIEF SUMMARY OF THE INVENTION

The 'NJA151' variety is distinguished from other apricot varieties due to the following unique combination of characteristics:

Attractive round fruit that are only slightly compressed.

Fruit with an attractive dark orange ground color.

Good production of fruit that ripen in early-season.

Fruit have above average eating quality with an average of 17% soluble solids.

The variety was asexually reproduced at the research farm in Cream Ridge, N.J. Asexual reproduction of this new variety by budding onto 'Lovell' peach rootstock (unpatented) shows that the foregoing characteristics are so reproduced.

The following detailed description concerns the original tree, 'NJA151'. The original tree and asexual progeny have been observed growing in a cultivated area at the research farm in Cream Ridge, N.J. Certain characteristics of this variety, such as growth and color, may change with changing environmental conditions (such as, light, temperature, moisture, nutrient availability) or other factors. Color descriptions and other terminology are used in accordance with their ordinary dictionary descriptions, unless the context clearly indicates otherwise. Color designations are made with reference to The Royal Horticultural Society (R.H.S.) Colour Chart.

BRIEF DESCRIPTION OF THE DRAWINGS

This new variety is illustrated by the accompanying photographic drawings, depicting the apricot tree by the best possible color representation using color photography. The colors of and illustration of this type may vary with lighting and other conditions under which conditions and, therefore, color characteristics of this new variety should be determined with reference to the observations described herein, rather than from these illustrations alone.

DETAILED BOTANICAL DESCRIPTION

Figure 1:
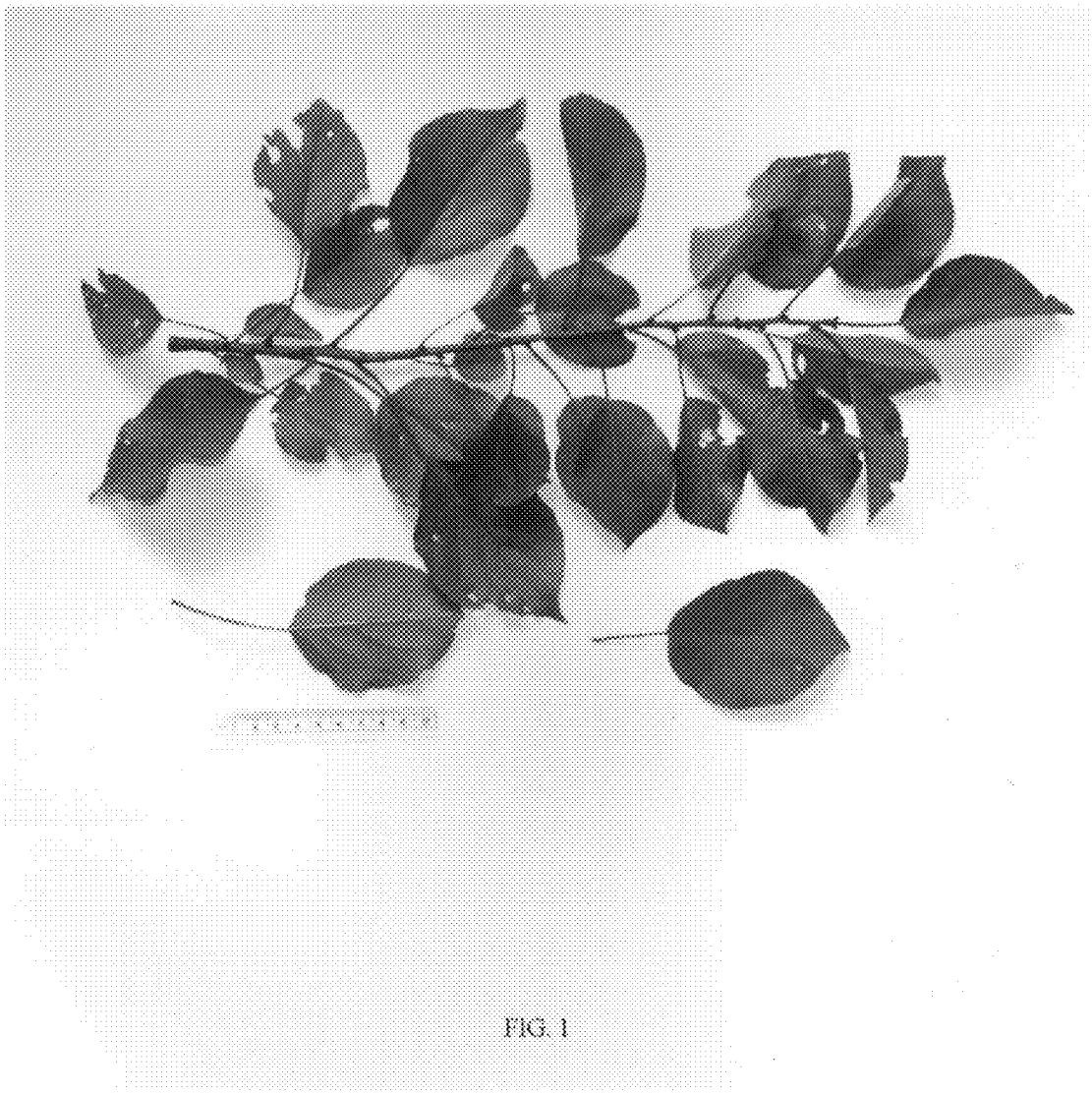
FIG. 1 is a color photograph taken on Oct. 14, 2011 of a characteristic twig of 'NJA151' in late summer bearing typical leaves of the mature and immature foliage.
Figure 2:
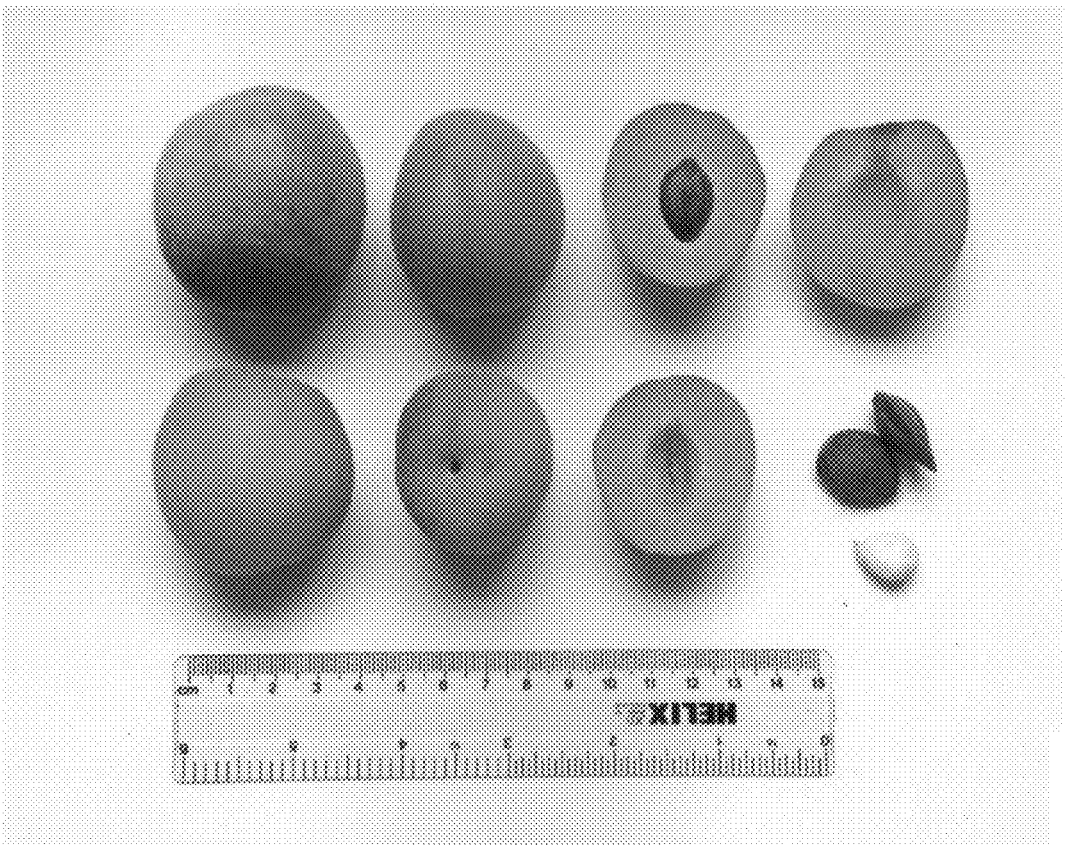
FIG. 2 is a color photograph taken on Jun. 19, 2012 of characteristic mature fruit, stones and fresh kernels of 'NJA151'. Whole fruit are presented in four positions and transverse and longitudinal sections to illustrate the orange flesh color and pericarp that does not adhere to the stone.
Figure 3:
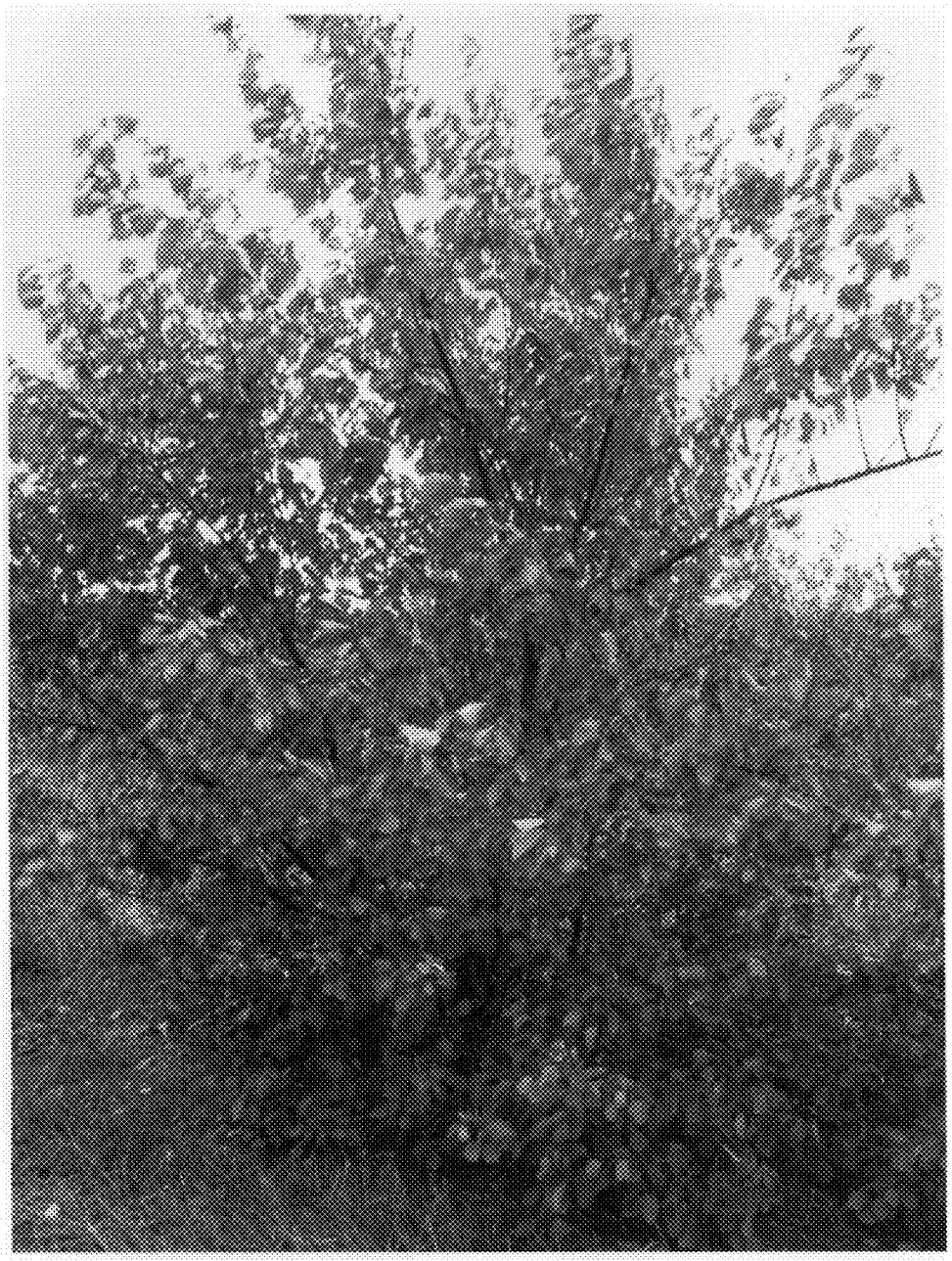
FIG. 3 is a color photograph of a tree of 'NJA151' in early fall that illustrates the spreading to slightly upright growth habit of a tree at the research farm in Cream Ridge, N.J. on Oct. 14, 2011.
Figure 4:
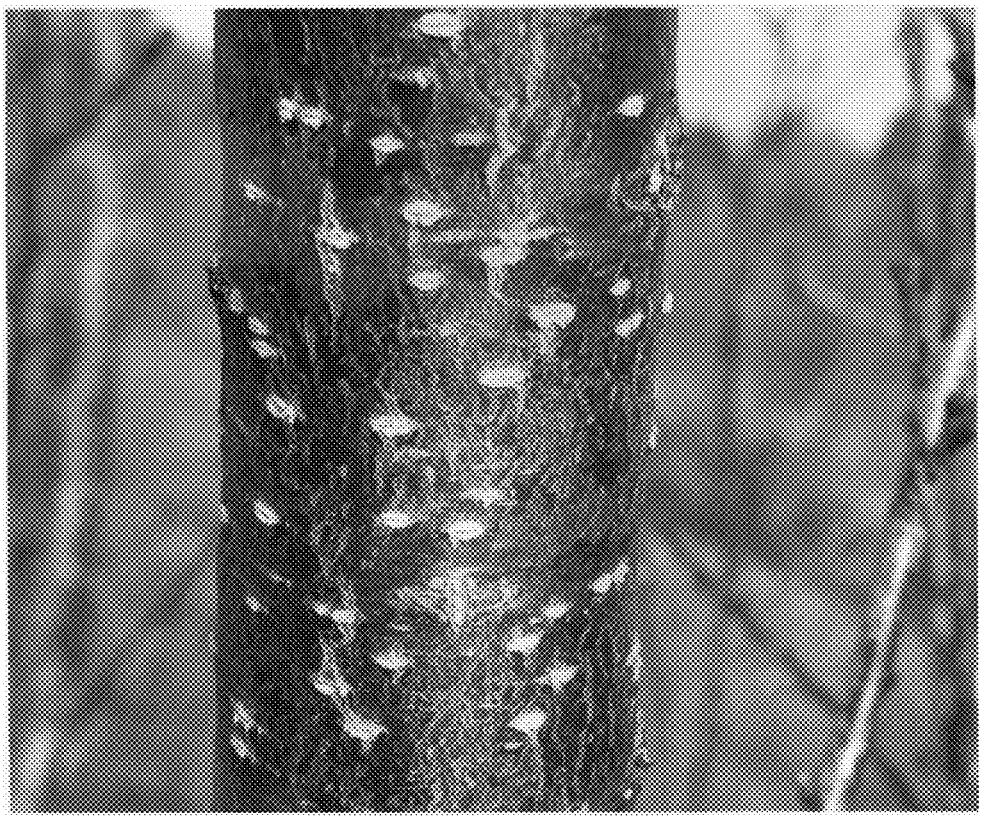
FIG. 4 is a color photograph taken on Dec. 22, 2011 of immature bark of 'NJA151' that illustrates color and the low density of elliptical greyed-white lenticels on the immature bark.
Figure 5:
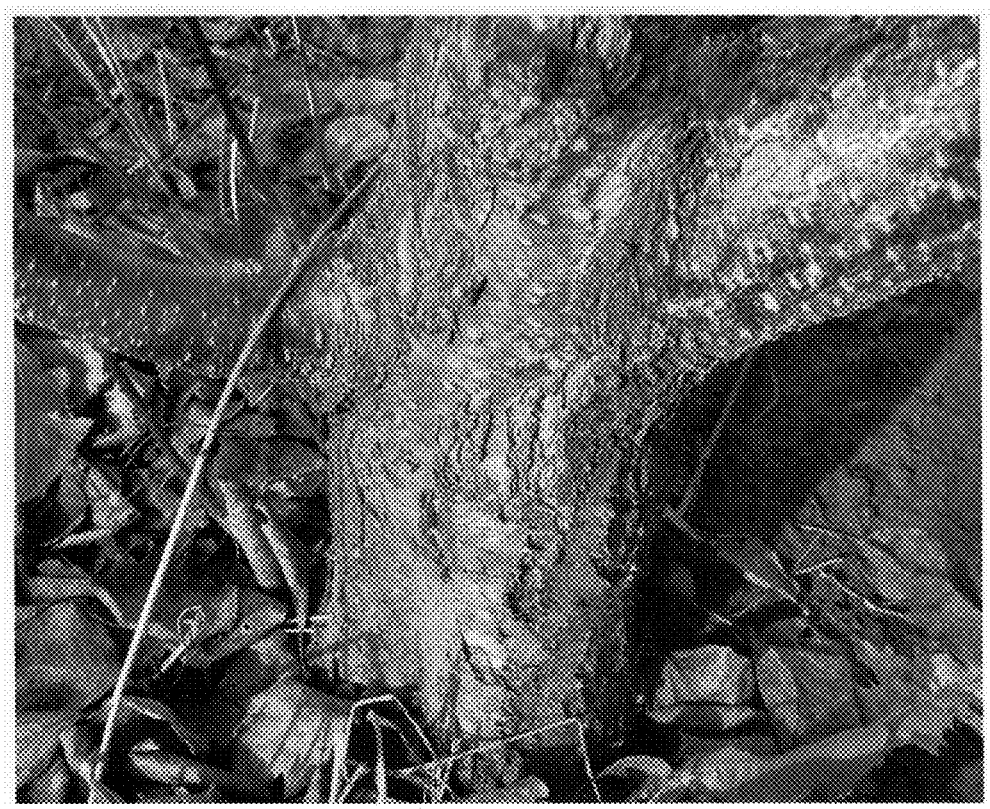
FIG. 5 is a color photograph taken on Dec. 22, 2011 of mature bark of 'NJA151' that illustrates the moderately rough texture of the mature bark.
Figure 6:
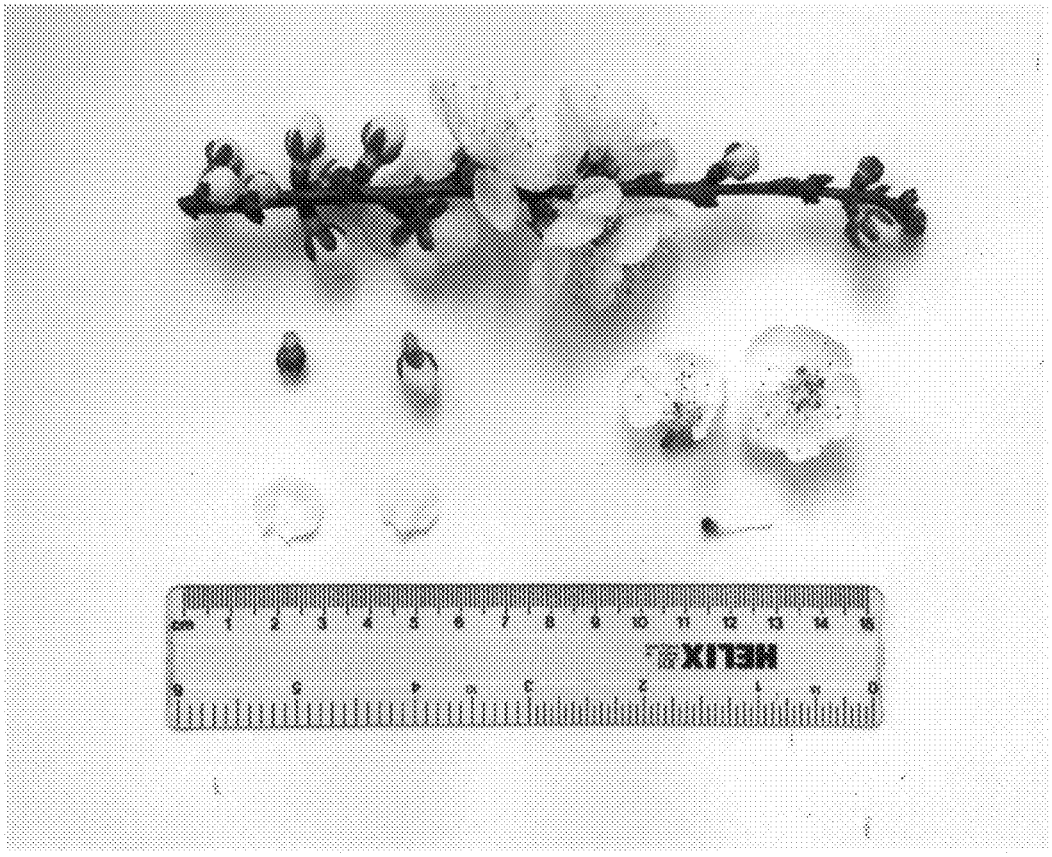
FIG. 6 is a color photograph taken on Mar. 20, 2012 of a characteristic twig of 'NJA151' that illustrates the typical flower buds and showy flowers of 'NJA151'.

The following detailed description of the 'NJA151' variety is based on observations of a budded tree. The observed tree was five years of age and growing on 'Lovell' peach rootstock in Research Block C at the research farm in Cream Ridge, N.J.

Scientific name: *Prunus persica* L.

Parentage:

| | |
|---|---|
| Seed parent: | 'Harcot' |
| Pollen parent: | 'Bhart' |

Tree:

| | |
|---|---|
| Vigor: | Vigorous. |
| Plant hardiness zone: | Growth of plants has only been observed in zone 6b. |
| Dormant flower bud cold tolerance: | At least to −20° C. |
| Overall shape: | Spreading to slightly upright. |
| Height: | Above average as compared to other apricot cultivars. For example, measurement of a typical tree at five years after planting shows an average height of 4 meters when grown in Cream Ridge, New Jersey. |
| Width: | Average as compared to other apricot cultivars. For example, measurement of a typical tree at five years after planting shows an average width of 4 meters when grown in Cream Ridge, New Jersey. |
| Caliper: | Five year old tree is 39 cm in circumference measured at 15 cm from the ground. |

Trunk and branches:

| | |
|---|---|
| Trunk bark texture: | Moderately rough. |
| Trunk bark color: | Greyed-green (between RHS 197a and RHS 197b). |
| Primary branches: | Branches that are approximately 15 cm in circumference are greyed-orange (between RHS 176b and RHS 177a) in color. |
| Lenticels: | Low density, approximately 0.85 per square cm; elliptical shape; typical examples of which measured 3.6 mm in length and 1.9 mm in width; orange-white (between RHS 159a and RHS 159b) in color, with a greyed-white border (RHS 156b). |
| Branch pubescence: | None. |

-continued

| | |
|---|---|
| New growth bark: | Greyed-orange (RHS 176a) in sun to greyed-orange (between RHS 165a and RHS 166a) in shade. |
| Texture: | Nearly smooth to slightly rough with prominent raised lenticels. |
| Internodes: | Length averaging 16.5 mm on a one-year shoot. |

Leaves:

| | |
|---|---|
| Texture: | Glabrous. |
| Sheen: | Mature leaves semi-glossy with a flat finish on the underside. |
| Length: | About 101 mm to 164 mm, averaging about 131 mm including the petiole. |
| Width: | About 67 mm to 78 mm, averaging about 73 mm. |
| Petiole: | About 44 mm in length and about 2.0 mm in diameter. |
| Margin: | Senate. |
| Margin undulation: | Nearly none. |
| Form: | Ovate. |
| Apex: | Acuminate and curved downward. |
| Base: | Broadly obtuse to truncate. |
| Venation: | Pinnate. |
| Glands: | |
| Number: | About 1 to 4, averaging about 2.5. |
| Position: | Located on the petiole. |
| Size: | Length averaging 0.8 mm and width averaging 0.8 mm. |
| Form: | Globose. |
| Stipules: | None observed on mature leaves. |
| Leaf Color: | |
| Upper leaf surface: | Yellow-green (between RHS 146b and RHS 146c). |
| Lower leaf surface: | Yellow-green (between RHS 147b and RHS 147c). |
| Vein: | Greyed-yellow (RHS 160c). |
| Petiole: | Greyed-purple (RHS 185a). |
| Pubescence: | None. |

Flowers:

| | |
|---|---|
| Dormant bud | Ovoid in shape, measuring about 4.5 mm in length and 2.6 mm in diameter. |
| Color: | |
| Dormant bud: | Brown (RHS 200a). |
| Pink stage bud: | Red-purple (between RHS 62b and RHS 62c). |
| Open flower: | Young open flowers red (between RHS 56c and RHS 56d) becoming white (RHS 155d) prior to petal fall. |
| Size | Large size, typical flower measuring between 24.9 mm to 32.2 mm, averaging about 28.1 mm across. |
| Petals: | Typically five petals per flower; cupped and round in shape; averaging about 13.6 mm long and 14.0 mm wide. Upper and lower surfaces of young petals are red (RHS 56d) with red (RHS 56c) margins becoming white (RHS 155d) prior to petal fall. |
| Petal margin: | Entire. |
| Petal apex: | Rounded. |
| Petal base: | Acute. |
| Stamens: | |
| Number: | Variable, 26 to 33, averaging about 29. |
| Length: | Variable, between 8.8 mm to 12.5 mm, averaging 11.0 mm. |
| Filament color: | White (RHS 155c). |
| Anther color: | Yellow-green (RHS 153d). |
| Pistil: | |
| Number: | One. |
| Size: | Length between 14.0 and 17.6 mm, averaging about 15.8 mm. |
| Pistil color: | Yellow-green (RHS 145c). |
| Ovary: | Ellipsoid in shape and covered with moderate pubescence. |

-continued

| | |
|---|---|
| Sepals: | |
| Number: | Five. |
| Pubescence: | None. |
| Color: | Exterior surface is greyed-purple (RHS 183d), interior surface is yellow-green (between RHS 150c and RHS 150d) overlayed with greyed-purple (between RHS 186c and RHS 186d). |
| Shape: | Triangular, with a rounded apex. |
| Margin: | Entire. |
| Size: | Length averaging 5.3 mm, width averaging 4.4 mm. |
| Nectar cup color: | Greyed-orange (RHS 167a). |
| Pollen: | Abundant; yellow-orange (RHS 20a) in color. |
| Fragrance: | Slight. |
| Bloom season: | Onset of bloom in 2011 on April 6; full bloom on April 8. |

Fruit:

| | |
|---|---|
| Size: | Medium, averaging about 4.5 cm long, 4.4 cm wide parallel to the suture and 3.9 cm wide perpendicular to the suture. |
| Typical weight: | 40 g. |
| Form: | |
| Longitudinal section: | Round, slightly oblong. |
| Traverse section: | Generally elliptical, some fruit may be slightly ovate. |
| Suture: | Shallow but distinct, extending from the base to apex. |
| Base: | Flat. |
| Apex: | Generally flat. |
| Stem: | Average length of 7.0 mm and an average diameter of 3.2 mm. |
| Stem color: | Greyed-orange (between RHS 164a and RHS 164b). |
| Skin: | |
| Thickness: | Average. |
| Surface: | Regular with short pubescence. |
| Tenacity: | Average. |
| Astringency: | None. |
| Tendency to crack: | Low. |
| Color: | Freckled red (RHS 46a) with a red (between RHS 45a and RHS 44b) blush over an orange (RHS 25b) ground color. |
| Fruit Properties: | |
| Flesh color: | Orange (between RHS 25a and RHS 25b). |
| Flesh adhesion: | Freestone. |
| Juice: | Moderate. |
| Texture: | Fine, melting. |
| Fibers: | Not noticeable. |
| Harvest dates: | First picking date ranges between June 18 and June 30 at Cream Ridge, New Jersey. Last picking date is generally two to three days after the first picking date. |

-continued

| | |
|---|---|
| Flavor: | Above average, fully flavored and aromatic when soft ripe. |
| Soluble solids: | 16%. |
| Aroma: | Moderate. |
| Eating quality: | Very good. |
| Keeping quality: | Average. Fruit held in cold storage has maintained firmness and quality for over one week. |
| Shipping quality: | Average. |
| Usage: | Desert. |
| Market: | Fresh market. |
| Productivity: | Very good. Trees have produced a crop in five out of five years and a full crop in three out of five years at Cream Ridge, New Jersey. |

Stone:

| | |
|---|---|
| Type: | Freestone. |
| Form: | Nearly round, but slightly elliptic. |
| Base angle: | Medium. |
| Apex angle: | Medium. |
| Surface: | No prominent markings. |
| Ridge: | High flanked by shallow lines, extending from the base to the apex. |
| External color: | Greyed-orange (between RHS 165b and RHS 165c). |
| Internal color when cracked: | Greyed-orange (165c). |
| Cavity surface color: | Greyed-orange (between RHS 165c and RHS 165d). |
| Average stone dry weight: | 1.4 g. |
| Average stone wall thickness: | Varies between 1.5 and 4.0 mm. |
| Size: | Averages about 22.46 mm long, 18.5 mm wide parallel to the dorsal ridge, and 11.2 mm wide perpendicular to the dorsal ridge. |
| Tendency to split: | Low. |
| Kernel: | |
| Form: | Ovate. |
| Skin color: | Greyed-orange (RHS 165c). |
| Vein color: | Greyed-orange (RHS 165b). |
| Viability: | Yes. |
| Dry weight | 0.3 g |
| Size: | Averages about 14.3 mm long, 9.7 mm wide, and 4.1 mm in breadth. |

Plant/fruit disease and pest resistance/susceptibility: No atypical resistance/susceptibilities have been noted under normal cultural practices.

We claim:

1. A new and distinct variety of apricot tree, substantially as herein illustrated and described.

* * * * *